United States Patent [19]

Gorun et al.

[11] Patent Number: 4,869,838

[45] Date of Patent: Sep. 26, 1989

[54] BIS IMIDAZOLE ETHERS AS METAL DEACTIVATORS

[75] Inventors: Sergiu M. Gorun, Upper Montclair; John W. Frankenfeld, Hoboken, both of N.J.

[73] Assignee: Exxon Research and Engineering Company, Florham Park, N.J.

[21] Appl. No.: 236,573

[22] Filed: Aug. 25, 1988

[51] Int. Cl.$^4$ ................. C10M 105/56; C07D 233/64
[52] U.S. Cl. ........................... 252/51.5 R; 252/56 R; 548/336
[58] Field of Search ...................... 548/336; 252/47.5

[56] References Cited

U.S. PATENT DOCUMENTS

| | | | |
|---|---|---|---|
| 2,352,164 | 6/1944 | Burnham et al. | 252/42.7 |
| 2,547,497 | 4/1951 | Rowland | 260/101 |
| 2,713,582 | 7/1955 | Smith | 548/352 |
| 2,713,583 | 7/1955 | Smith | 548/348 |
| 3,024,236 | 3/1962 | Hughes | 544/296 |
| 3,096,294 | 7/1963 | Hughes | 252/390 |
| 3,138,610 | 6/1964 | Buc et al. | 548/348 |
| 3,360,506 | 12/1967 | DeBenneville et al. | 526/263 |
| 3,408,297 | 10/1968 | Sheldahl | 252/33.3 |
| 3,473,901 | 10/1969 | DeBenneville et al. | 44/62 |
| 4,392,968 | 7/1983 | Ishida et al. | 252/51.5 R |

OTHER PUBLICATIONS

S. Gorun et al, *Inorganic Chemistry*, 1988, 27, 149.

*Primary Examiner*—Richard A. Schwartz
*Attorney, Agent, or Firm*—Joseph J. Dvorak

[57] ABSTRACT

Bis imidazole ethers have been found to be effective metal deactivators. Thus, one aspect of the present invention comprises novel bis imidazole ethers of the formula:

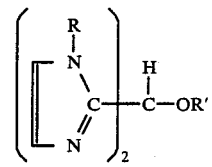

in which R is a normal alkyl group having from 1 to 12 carbon atoms and R' is a normal alkyl group having from 1 to carbon atoms, an alkylaryl group having from 7 to 20 carbon atoms, or an aryl group of 6 to 10 carbon atoms. In another aspect of the present invention, an improved lubricating oil is provided comprising a base lubricating oil and the bis imidazole ethers of this invention.

9 Claims, No Drawings

BIS IMIDAZOLE ETHERS AS METAL DEACTIVATORS

FIELD OF THE INVENTION

This invention relates to novel bis imidazole ethers and methods for their preparation. This invention also relates to uses of these compounds as metal deactivators in lubricants.

BACKGROUND OF THE INVENTION

Oxidation stability is a major requirement for all industrial lubricants. The major cause of oxidative instability is the autoxidative breakdown of the hydrocarbons in the lubricants with the concomitant formation of acids and other undesirable oxygenated species as well as sludge. Such autoxidative breakdown is strongly catalyzed by traces of metal ions, especially copper and iron, which become solubilized when the lubricant comes in contact with metal surfaces. One way to control oxidation is to incorporate into the lubricant certain additives, called metal deactivators, which prevent these catalytic reactions from occurring. Metal deactivators generally work in two different ways; they form impervious films on the metal surface, thereby preventing dissolution of the metal ions, and hence are called "film forming" additives, or they form chelates with the solubilized metal ions, thus rendering them inactive as catalysts, and hence are called "soluble metal chelators". Examples of the use of metal deactivators to stabilize lubricating compositions can be found, for example, in U.S. Pat. Nos. 2,352,164 and 4,392,968.

It is an object of this invention to provide new and improved metal deactivators having superior performance over that of conventional metal deactivators.

It is also another object of the present invention to provide compositions containing a new metal deactivator.

SUMMARY OF THE INVENTION

Briefly stated, the present invention is predicated on the discovery that novel bis imidazole ethers have been found to be effective metal deactivators. Thus, one aspect of the present invention comprises novel bis imidazole ethers of the formula:

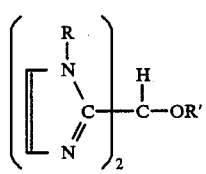

in which R is a normal alkyl group having from 1 to 12 carbon atoms and R' is a normal alkyl group having from 1 to 12 carbon atoms, an alkylaryl group having from 7 to 20 carbon atoms, or an aryl group of 6 to 10 carbon atoms.

In another aspect of the present invention, there is provided a method for preparing the above-mentioned compounds.

In yet another aspect of the present invention, novel compositions are provided comprising a base lubricating oil, such as mineral oils and synthetic oils, and an effective amount of a metal deactivator comprising at least one member selected from the bis imidazole ethers having the formula:

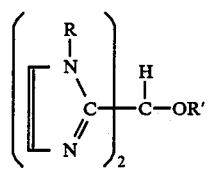

wherein R is a normal alkyl group of from 1 to 12 carbon atoms and R' is a normal alkyl group having from 1 to 12 carbon atoms, an alkylaryl group having from 7 to 20 carbon atoms, or an aryl group of 6 to 10 carbon atoms. Preferably R is methyl and R' n-octyl.

These and other aspects of the present invention will be described in detail in the "Preferred Embodiments of the Invention" which follows.

PREFERRED EMBODIMENTS OF THE INVENTION

The novel bis imidazole ethers of the present invention are represented by the formula:

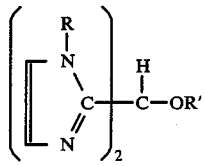

wherein R is a normal alkyl group having from 1 to 12 carbon atoms, and R' is a normal alkyl group of from 1 to 12 carbon atoms, an aryl group of 6 to 10 carbon atoms, or an alkylaryl group of 7 to 20 carbon atoms.

The compounds of the present invention are made by reacting bis[(N-alkyl) imidazol-2-yl] carbinol with a source (M) of an alkali metal ion so as to form the alkoxide of the imidazole carbinol (see Equation 1) and thereafter reacting the alkoxide with an organic halide (R'X), such as a chloride, bromides or iodide, in which the organic portion of the halide is an alkyl, aryl or alkylaryl group corresponding to R' as defined above (see Equation 2).

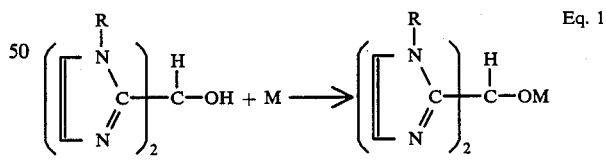

Eq. 1

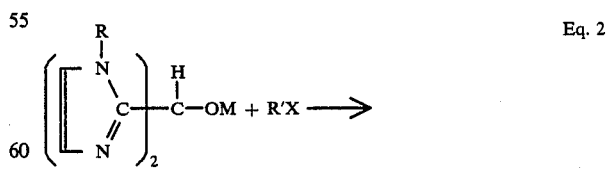

Eq. 2

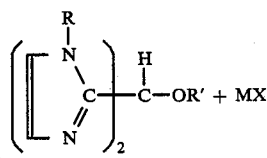

Among the suitable sources of alkali metal ions include the alkali metals themselves, sodium and potassium for example, metal hydrides such as sodium hydride, and alkali metal alkoxides such as potassium tertiary butoxide. Indeed, it is particularly preferred in the practice of the present invention to react the bis [(N-alkyl) imidazol-2-yl] carbinol with tertiary butoxide in a suitable solvent.

Among solvents suitable in the practice of the present invention are tetrahydrofuran, diethylether, tertiary butanol and higher molecular weight ethers. In the practice of the present invention, it is particularly preferred to use tetrahydrofuran as the solvent.

In general, the reaction may be carried out over a wide temperature range, for example, from 10° C. to about 100° C. However, it has been generally found adequate to carry out the reaction at ambient temperature conditions.

The bis imidazole ethers of the present invention are useful as metal deactivators for lubricants. Basically, it is believed that the bis imidazole ethers of the present invention operate to chelate metal ions, especially copper and iron ions in lubricating oils. Thus, compositions of this invention comprise a lubricating oil selected from the group consisting of mineral oils and synthetic oils and an effective amount of a metal deactivator selected from the group consisting of compounds or mixtures thereof represented by the formula:

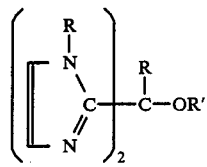

wherein R is a normal alkyl group of from 1 to 12 carbon atoms and R' is a normal alkyl group having from 1 to 12 carbon atoms, an alkylaryl group having from 7 to 20 carbon atoms, or an aryl group of 6 to 10 carbon atoms.

The mineral oils and synthetic oils of the compositions of the present invention will, of course, have lubricating viscosities, for example, viscosities in the range of about 1.0 centistoke to 1800 centistokes at 40° C., and preferably in the range of 2.0 to 1600 centistokes. A typical mineral oil used in the compositions of the present invention consists of a commercially available mineral oil known as Solvent 150 Neutral. Preferred examples of synthetic oils include polyalphaolefins and polyolesters.

As indicated, the amount of metal deactivator generally is sufficient to stabilize the lubricating oil against autoxidation. In general, the amount of metal deactivator will be in the range of about 0.01 to 5.0 percent by weight based on the total weight of composition, preferably in the range of about 0.05 to 1.0 percent by weight.

The following examples will serve to further illustrate the invention.

EXAMPLES

EXAMPLE 1

This Example illustrates one method of preparing a novel bis imidazole ether of the present invention. To 1.4 grams (12.5 mmoles) of potassium t-butoxide dissolved in 360 ml of dry tetrahydrofuran was added 1.55 grams (8.1 mmoles) of bis [(N-methyl)imidazol-2-yl]carbinol. A white precipitate appeared in about ten minutes. Then 3.3 ml (19 mmoles) of octyl bromide was added dropwise. The reaction mixture was stirred overnight and then quenched with 50% saturated aqueous sodium chloride. The organic layer was separated, dried, and the solvent removed under vacuum. The crude material was obtained in over 90% yield s judged by NMR. It was subsequently purified by extraction in hexane. Elemental analysis showed: carbon, 58.24%; hydrogen, 6.84%; nitrogen, 27.16%. Calculated for the octyl ether of bis[(N-methyl)imidazol-2-yl]carbinol (BICO-OCT): carbon, 57.98%; hydrogen, 7.15%; nitrogen, 27.41%. The compound was further identified by mass spectroscopy and NMR.

EXAMPLE 2

In this example 1.4 grams (12.48 m moles) of potassium t-butoxide was dissolved in 360 ml of dry THF. Then 1.55 grams (8.1 mmoles) of bis [(N-methyl)imidazol-2] carbinol was added and the mixture was stirred for about 40 minutes. A white precipitate formed however, in about 10 minutes. Next 2.736 grams (19.1 mmoles) of 99% methyliodide was added dropwise. The mixture was stirred overnight and quenched with 80 ml (50% saturated) aqueous NaCl solution. The organic layer was separated and the solvents removed under reduced pressure. The residue has extracted with methylene chloride and the extract dried over $K_2CO_3$. The methylene chloride solution was then rotoevaporated to provide a yellow solid which was boiled in 550 ml of cyclohexane for 60 hours. The cyclohexane was decanted and rotoevaporated to yield 1.12 grams of a white crystalline solid. Elemental analysis showed: carbon, 57.98%; hydrogen, 7.15%; and nitrogen 27.41%. Calculation for the methyl ether of bis[(N-methyl)imidazol-2yl] carbinol: carbon, 58.24% hydrogen, 6.84%; 27.16%.

The compound was also characterized by NMR.

EXAMPLE 3

This Example illustrates the utility of bis [(N-methyl)imidazol-2-yl] carbinol octyl ether (BICO-OCT), and bis[(N-methyl)imidazol-2] carbinol methyl ether (BICO-Me) as metal deactivators for lubricants.

In this example, BICO-OCT and BICO-Me are shown to be effective metal deactivators by the ASTM D2440 Test, the CIGRE (IP 280) Test and the Universal Oxidation Test (UOT). Each of these tests are standard tests for evaluating additives that are well known in the art. All tests were conducted in a base lubricating oil consisting of Solvent 150 Neutral containing 0.2 wt % Parabar 441 and 0.4 wt % Parabar 302. Parabar 441 is a Registered Trademark for a phenolic antioxidant containing 2,6 di-t-butyl phenol sold by Exxon Chemical Company, Darien, Conn. and Parabar 302 also is a Registered Trademark of Exxon Chemical Company for a rust inhibitor containing tetrapropenyl succinic acid and the mono ester of that acid formed with propane diol. For comparative purposes, one run was conducted without a metal deactivator and one with a commercially available metal deactivator.

(a) ASTM D2440 Oxidation Test

These tests were performed at 120° C. for 164 hours using a solid copper wire catalyst (oxygen flow rate=1 liter per hour). Dissolved copper concentrations and the total oxidized products (TOP) were determined at the end of the test. TOP is determined by measuring the total acid number (TAN) and the sludge produced by the test. The TOP is defined as TOP:

$$TOP = \frac{TAN \text{ (mg KOH/g)}}{3} + wt \% \text{ sludge}$$

The lower the TOP the better the additive functions as an antioxidant or metal deactivator. The data are given in Table I:

TABLE I
Results of D2440 Tests

| Metal Deactivator | Conc. Wt % | Dissolved Cu (ppm) | TOP (wt %) |
|---|---|---|---|
| None (1) | — | 19.5 | 1.0 |
| Reomet-39 (2) | 0.08 | 1.7 | 0.2 |
| BICO-OCT | 0.06 | 4.1 | 0.1 |
| BICO-Me | 0.04 | 3.6 | 0.1 |

(1) Contains Parabar additives.
(2) Commercial metal deactivator of the benzotriazole type sold by Ciba-Geigy, Greensboro, North Carolina.

BICO-OCT and BICO-me and excellent antioxidants as shown by its low TOP, significantly than the value obtained for a typical commercial metal deactivator. The fairly high soluble copper value indicates that these new additives serve largely as a soluble metal chelators rather than film formers.

(b) CIGRE (IP 280) Tests

The CIGRE test measures the ability of additives to deactivate soluble copper and iron. Film former additives, which may be effective versus solid metals in the D2440 Test, do not perform well in the CIGRE. The CIGRE Test is carried out at 120° C. for 164 hours with soluble copper naphthenate, soluble iron naphthenate or a combination of the two as catalysts. An oxygen flow rate of 1½ hours is maintained. Results are given in Table II:

TABLE II
CIGRE Test Results

| Additive | Conc., wt % | TOP (Wt %) vs Cu | Fe | Cu + Fe |
|---|---|---|---|---|
| None (1) | — | 2.1 | 2.4 | 4.0 |
| Reomet-39 (2) | 0.08 | 2.2 | 2.3 | 5.1 |
| BICO-OCT | 0.06 | 0.1 | 0.5 | 2.0 |
| BICO-Me | 0.04 | 0.2 | 0.6 | 2.3 |

(1) Contains Parabar additives.
(2) Commercial metal deactivator of the benzotriazole type sold by Ciba-Geigy, Greensboro, North Carolina.

These data show that the bis imidazole ethers of the present invention are effective antioxidants against soluble copper and iron.

(c) Universal Oxidation Test (UOT)

This is a high temperature oxidation test designed to determine the effectiveness of additives against a mixture of solid copper and iron catalysts. The test is conducted at 135° C. Air is blown through the oil at a rate of 3.0 l/hr. A water condenser is employed to condense volatile products. The effectiveness of the antioxidant is determined by measuring the time required for the acid titer of the oil to increase by 0.5 neutralization numbers (0.5 NN) The longer the lifetime the more effective the antioxidant. Results are shown in Table III:

TABLE III
UOT Test Results

| Additive | Conc., wt % | UOT Life (3) (Hrs) |
|---|---|---|
| None (1) | — | 45 |
| Reomet-39 (2) | 0.08 | 115 |
| BICO-OCT | 0.06 | 558 |
| BICO-Me | 0.04 | 509 |

(1) Contains Parabar additives.
(2) Commercial metal deactivator of the benzotriazole type sold by Ciba-Geigy, Greensboro, NC.
(3) Defined as time to 0.5 NN increase.

These data show that the imidazole ethers of this invention are effective antioxidants.

What is claimed is:

1. A bis imidazole ether of the formula:

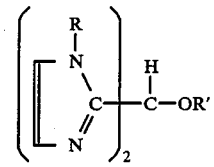

wherein R is a normal alkyl group having from 1 to 12 carbon atoms and R' is a normal alkyl group having from 7 to 12 carbon atoms, an alkylaryl group having from 7 to 20 carbon atoms, or an aryl group of 6 to 10 carbon atoms.

2. The ether of claim 1 wherein R is methyl.
3. The ether of claim 1 or 2 wherein R' is octyl.
4. The ether of claim 1 or 2 wherein R' is methyl.
5. A composition comprising a lubricating oil and an effective amount of a metal deactivator, said lubricating oil being selected from mineral oils and synthetic oils of lubricating viscosity, said metal deactivator being selected from compounds or mixtures thereof having the formula:

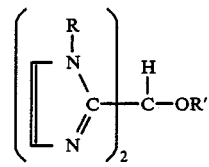

wherein R is a normal alkyl group having from 1 to 12 carbon atoms and R' is an alkyl group having from 1 to 12 carbon atoms, an alkaryl group having from 7 to 20 carbon atoms, or an aryl group of 6 to 10 carbon atoms.

6. The composition of claim 5 wherein said activator is present in amounts ranging from about 0.01 wt % to about 5.0 wt % based on the total weight of the composition.

7. The composition of claim 6 wherein said activator is present in amounts ranging from about 0.05 wt % to about 1.0 wt % based on the total weight of the composition.

8. The composition of claim 6 wherein R in said formula is methyl and R' is octyl.

9. The composition of claim 6 wherein R is methyl and R' is methyl.

* * * * *